United States Patent

Albrecht et al.

[11] 3,952,014
[45] Apr. 20, 1976

[54] BIS-BASIC ESTERS AND AMIDES OF DIBENZOTHIOPHENE

[75] Inventors: William L. Albrecht; Robert W. Fleming, both of Cincinnati, Ohio

[73] Assignee: Richardson-Merrell Inc., Wilton, Conn.

[22] Filed: Aug. 18, 1969

[21] Appl. No.: 851,098

[52] U.S. Cl. ............ 260/329.3; 260/326.25; 260/293.57; 260/268 TR; 260/247.1 P; 424/274; 424/267; 424/250; 424/248
[51] Int. Cl.² .................................. C07D 333/76
[58] Field of Search ........................... 260/329.3

[56] References Cited
OTHER PUBLICATIONS
Gilman et al., J.A.C.S. 61: 1371–1373 (June 1939).
Burtner et al., J.A.C.S. 62: 527–532 (1940).
Hartough et al., Compounds with Condensed Thiophene Rings, (Interscience, New York, 1954), pp. 268–273.

Primary Examiner—Henry R. Jiles
Assistant Examiner—C. M. S. Jaisle
Attorney, Agent, or Firm—George W. Rauchfuss, Jr.; Eugene O. Retter

[57] ABSTRACT
Novel bis-basic esters and amides of dibenzothiophene of the formula

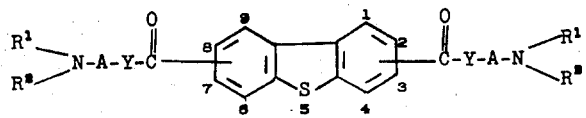

wherein:
A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;
B. each A is alkylene of 2 to about 8 carbon atoms and separates its adjacent Y and amino nitrogen by an alkylene chain of at least 2 carbon atoms;
C. each Y is oxygen, or N—R wherein R is hydrogen or (lower)alkyl of 1 to 4 carbon atoms; or a pharmaceutically acceptable acid addition salt thereof. These compounds can be used as pharmaceuticals for preventing or inhibiting a viral infection.

6 Claims, No Drawings

BIS-BASIC ESTERS AND AMIDES OF DIBENZOTHIOPHENE

This invention relates to novel bis-basic esters and amides of dibenzothiophene, their method of preparation and use as antiviral agents.

Dibenzothiophene-2,8-dicarboxylic acid[1] was prepared by the Grignard Reaction from 2,8-dibromodibenzothiophene in 1928. However, to applicants' knowledge, the bis-basic substituted esters or amides of dibenzothiophene are novel compounds.

[1] C. Courtot, L. Nicolas and T. H. Liang, Comp. rend. 186,1624 (1928)

The compounds of this invention include both the base form and pharmaceutically acceptable acid addition salts of the base form wherein the base form can be represented by the formula

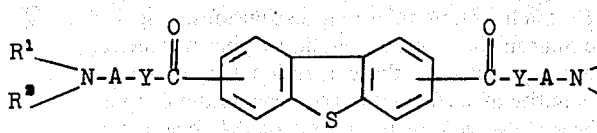  Formula I wherein:

A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;

B. each A is alkylene of 2 to about 8 carbon atoms and separates its adjacent Y and amino nitrogen by an alkylene chain of at least 2 carbon atoms;

C. each Y is oxygen, or N-R wherein R is hydrogen or (lower)alkyl of 1 to 4 carbon atoms; or a pharmaceutically acceptable acid addition salt thereof.

Each of the alkylene groups as represented by A in the above generic Formula I is an alkylene group having from 2 to about 8 carbon atoms which can be straight chained, or branched chained and which separates its adjacent Y from the amino nitrogen by an alkylene chain of at least two carbon atoms. Thus, the Y group and the amino nitrogen are not on the same carbon atom of the alkylene group. Each of the alkylene groups as represented by A can be the same of different. Preferably both of these groups are the same. Illustrative of alkylene groups as represented by A there can be mentioned: 1,2-ethylene; 1,3-propylene; 1,4-butylene; 1,5-pentylene; 1,6-hexylene; 2-methyl-1,4-butylene; 2-ethyl-1,4-butylene; 3-methyl-1,5-pentylene; 2,2-dimethyl-1,5-pentylene and the like. Preferably, A is alkylene having from 3 to 6 carbon atoms.

Each amino group, i.e.,

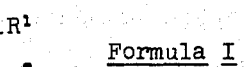

of Formula I, can be a primary, secondary or tertiary amino group. Each of $R^1$ and $R^2$ can be hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is a saturated monocyclic heterocyclic group.

Illustrative of cycloalkyl groups as represented by each of $R^1$ and $R^2$ there can be mentioned: cyclopropyl; cyclobutyl; cyclopentyl; cyclohexyl; and the like. When $R^1$ and $R^2$ represent alkenyl groups, the vinyl unsaturation is in other than the 1-position of said alkenyl group. Illustrative of alkenyl groups as can be represented by each of $R^1$ and $R^2$ there can be mentioned: allyl; 3-butenyl; 4-hexenyl; and the like. Illustrative of heterocyclic groups represented by $R^1$ and $R^2$, together with the nitrogen atom to which they are attached, there can be mentioned various saturated monocyclic heterocyclic groups such as those generally equivalent to di(lower)alkylamino groups in the pharmaceutical arts, e.g., pyrrolidino, piperidino, morpholino, N-(lower)alkylpiperazino such as N-methylpiperazino; N-ethylpiperazino; and the like. Each of the $R^1$ and $R^2$ groups can be the same or different. Preferably all of the $R^1$ and $R^2$ groups are the same. The amino groups are preferably tertiary amino groups such as di(lower)alkylamino, dialkenylamino or each set of $R^1$ and $R^2$ together with the nitrogen to which they are attached is pyrrolidino, piperidino, N-(lower)alkylpiperazino or morpholino.

Each Y group in Formula I can be oxygen or N-R wherein R is hydrogen or (lower)alkyl of 1 to 4 carbon atoms. Preferably R is hydrogen.

The term (lower)alkyl or (lower)alkoxy as used herein relates to such groups having from 1 to 6 carbon atoms and preferably from 1 to 4 carbon atoms. Illustrative of (lower)alkyls as can be represented by each of $R^1$ and $R^2$ there can be mentioned straight or branched chain alkyls such as: methyl; ethyl; n-propyl; isopropyl; n-butyl; secondary butyl; tertiary butyl; isoamyl; n-pentyl; n-hexyl; and the like.

It can be seen from the generic Formula I and its description that the compounds of this invention can be (a) dibenzothiophene esters or (b) dibenzothiophene amides, which can be illustrated by the following formulas, respectively:

(a) ![structure] ; and

Formula II (b) 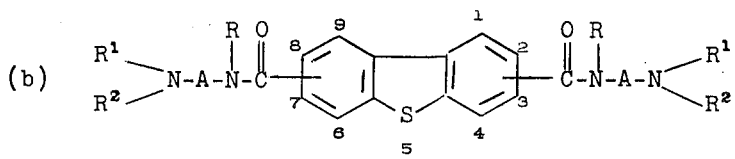

Formula III wherein R, R¹, R² and A have the same meaning as that in the description in Formula I.

Salts of the base compounds of this invention are primarily pharmaceutically acceptable acid addition salts with inorganic or organic acids. Illustrative of such acids there can be mentioned: hydrochloric, hydrobromic, sulfuric, lactic, malonic, maleic and citric acids. Mono- or di-acid salts can be formed; also, the salts can be hydrated, e.g., monohydrate, or substantially anhydrous.

The compounds of this invention, also referred to herein as active ingredients, can be used as antiviral agents for inhibiting or preventing a variety of viral infections by administering such an ingredient to an infected warm-blooded animal, e.g., a mammal, or to such animal prior to infection. The active ingredients induce the formation of interferon when host cells are subjected to such ingredients, e.g., contact of an active ingredient with tissue culture or administration to animals. It is known that interferon inhibits replication of certain viruses. Thus the compounds of this invention can be used to inhibit replication of those viruses susceptible to replication inhibition by interferon. This is accomplished by contacting the locus of a virus and host cells by the active ingredients of this invention.

Illustratively, the compounds can be administered to prevent or inhibit infections of: picornaviruses, e.g., encephalomyocarditis; myxoviruses, e.g., Influenza $A_0PR_8$; arboviruses; e.g., Semliki Forest; and poxviruses, e.g., Vaccinia, IHD. When administered prior to infection, i.e., prophylactically, it is preferred that the administration be within 24 or 48 hours prior to infection of the animal with pathogenic virus. When administered therapeutically to inhibit an infection, it is preferred that the administration be within about 24 or 48 hours after infection with pathogenic virus.

The daily dosage of the active ingredient can vary over a wide range such as that of from about 0.1 to 500 mg. (milligrams) per kg. (kilogram) of body weight and preferably from about 0.5 to about 100 mg/kg of body weight. The novel compounds together with conventional pharmaceutical carriers can be employed in unit dosage forms such as solids, for example, tablets or capsules, or liquid solutions, suspensions, or elixirs for oral administration and ingestion or liquid solutions, suspensions, emulsion and the like for parenteral use. The quantity of active ingredient in each dosage will generally differ depending on the type of unit dosage, the type of animal and its weight. Thus, each dosage can contain from about 1 mg. to 250 mg. of active ingredient in a significant quantity of pharmaceutical carrier.

A preferred mode of administration is parenterally such as by normally liquid injectable compositions, e.g., for intramuscular or subcutaneous administration. In such compositions the quantity of active ingredient can vary from about 0.05% to 20% by weight of the composition. The parenteral composition can be a solution, suspension or emulsion in conventional pharmaceutical carriers, e.g., sterile liquids such as water, saline, and aqueous dextrose (glucose) and related sugar solutions. In order to minimize or eliminate irritation at the site of injection, the parenteral compositions can contain a non-ionic surfactant such as those having an HLB (hydrophile-lipophile balance) of about 12 to 17. Such formulations can be solutions, suspensions or emulsions in conventional liquid pharmaceutical carriers, e.g., such as those mentioned hereinabove. The quantity of surfactant in the formulation can vary from about 5% to 15% by weight of the formulation. The quantity of a compound of this invention, either in the base form or a pharmaceutically acceptable acid addition salt in such formulations, can vary over a broad range such as that mentioned hereinbefore, i.e., 0.05% to 20% by weight of the formulation. Preferably, the active ingredient is in the base form. The remaining component or components of such formulations can be a normally liquid pharmaceutical carrier, e.g., isotonic aqueous saline, either alone or together with conventional excipients for injectable compositions. The surfactant can be a single surfactant having the above indicated HLB or a mixture of two or more surfactants wherein such mixture has the indicated HLB. The following surfactants are illustrative of those which can be used in such formulations: (A) polyoxyethylene derivatives of sorbitan fatty acid esters, such as the TWEEN series of surfactants, e.g., TWEEN 80, and the like. The TWEENS are manufactured by Atlas Powder Company. (B) High molecular weight adducts of ethylene oxide with a hydrophobic base formed by the condensation of propylene oxide with propylene glycol, e.g., PLURONIC F-68 which is manufactured by Wyandotte Chemical Company. The preferred surfactant is Polysorbate 80, U.S.P., a polyoxyethylene sorbitan monooleate.

The compounds of this invention can be prepared by a variety of procedures including the following:

1. A. The reaction of a dibenzothiophene dicarboxylic acid or a reactive derivative thereof such as an acid halide or ester of the formula

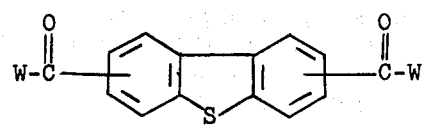

wherein W is hydroxy, halogen such as chlorine or bromine, or a lower alkoxy such as methoxy or ethoxy, with an aminoalkanol or aminoalkylamine of the formula

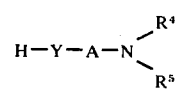

wherein Y is oxygen or N-R wherein R is hydrogen or (lower)alkyl of 1 to 4 carbon atoms, A is alkylene of 2 to about 8 carbon atoms, either straight chain or branched, and each $R^4$ and $R^5$ is (lower)alkyl, cycloalkyl of 3 to 6 ring carbon atoms, or alkenyl of 3 to 6 carbon atoms having the vinyl unsaturation in other than the 1-position of the alkenyl group, or together with the nitrogen to which they are attached form a heterocyclic group such as those generally equivalent to a di(lower)alkylamino group in the pharmaceutical arts.

B. The esterification can be achieved by allowing the dibenzothiophene dicarboxylic acid, where W in the above formula is hydroxy, to react with the appropriate aminoalkanol in an inert solvent in the presence of a catalyst and employing general methods for removing water from the reaction site. Preferred solvents are chloroform, isopropanol, dioxane, toluene and the like. The reaction may be catalyzed by the use of mineral acids including hydrochloric, sulfuric or certain organic acids such as p-toluenesulfonic acid. Methods whereby water can be removed from the reaction include the use of water scavengers such as the carbodiimides or by the azeotropic removal of water. The reaction will proceed at temperatures ranging from 50°–150°C. over a period of 6 to 72 hours depending upon the solvent and catalyst.

C. Preferably, the esterification can be achieved by allowing the acid halide, where W in the above formula is halogen, to react with the appropriate aminoalkanol. The esters of this invention can be produced in a variety of inert solvents over a wide range of temperatures and reaction time. The solvents of choice include chloroform, dioxane, tetrahydrofuran, and the aromatic solvents such as benzene and toluene. In chloroform, the reaction is generally complete within one hour at the reflux temperature of the solvent, although the reaction time can range from 15 minutes to 3 days. In like manner, the amides of this invention can be prepared by allowing the dibenzothiophene di-acid halide to react with the appropriate aminoalkylamine. The preferred reaction conditions are those which employ chloroform as the solvent and heating at the reflux temperature of said solvent for 3-18 hours.

D. The compounds of this invention may also be produced by a transesterification reaction in which a (lower)-alkoxy ester of the dibenzothiophene dicarboxylic acid, where W, for example, is methoxy or ethoxy in the above formula, is caused to react with the appropriate aminoalkanol under suitable conditions. This type of reaction is catalyzed by alkaline or acid catalysts and is reversible. The compounds of this invention may be produced by causing the equilibrium to be shifted by removing the lower alkanol component or by employing a large excess of the aminoalkanol. Preferably, the reaction is carried out by removing the lower alkanol component with the use of an alkaline catalyst. The lower alkanol may be removed by direct distillation or distillation with a suitable solvent. Suitable alkaline catalysts are alkali metals, sodium or potassium; alkali lower alkoxides, such as sodium methoxide or sodium ethoxide; alkali amides such as lithium or sodium amide; etc. Suitable solvents are those forming an azeotropic distillation mixture with the lower alkanol, for example, benzene or toluene, or a solvent which boils sufficiently higher than the alkanol to permit removal of the alkanol by distillation at a temperature below that of the boiling range of the solvent. The amides of this invention may also be produced by allowing the lower alkoxy ester of the dibenzothiophene dicarboxylic acid tor eact with the appropriate aminoalkylamine under the conditions as for the esters.

2. The esters of this invention can be produced by allowing the dibenzothiophene dicarboxylic acid, or an activated salt thereof, to react with an aminoalkyl halide in a suitable organic solvent such as chloroform or isopropanol. The aminoalkyl portion of the reactant is the same as in 1-A above. The reaction conditions can vary from 6 hours to 72 hours over a temperature range of from room temperature to the reflux temperature of the solvent employed in the presence or absence of an activating moiety such as inorganic cations including sodium and silver or organic activators such as benzyltrimethylammonium chloride. These activators may be present in stoichiometric amounts or catalytic quantities. Since these activators considerably reduce the reaction time, the preferred conditions are to use a catalytic amount o benzyltrimethylammonium chloride and allow the reaction to proceed for 6-18 hours at the reflux temperature of isopropanol.

3. The compounds of this invention can be prepared by allowing a dibenzothiophene ω-haloalkyl diester or diamide, prepared by general methods, of the formula:

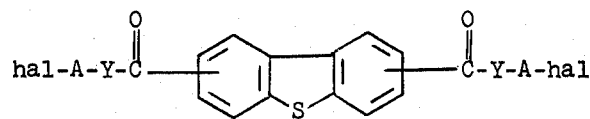

wherein Y and A are as previously defined in hal is chlorine, bromine or iodine to react with an amine of the formula

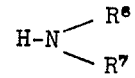

wherein $R^6$ and $R^7$ is (lower)alkyl, or together with the nitrogen to which they are attached form a heterocyclic group such as that generally equivalent to a dialkylamino group. The dibenzothiophene ω-haloalkyl diester or diamide may be prepared by the reaction of a dibenzothiophene dicarbonyl chloride with an ω- haloalkanol or an ω-haloalkylamine in a suitable solvent to give the respective products. The preferred halogen in the above formula is bromine or iodine. The reaction is conducted in the presence of stoichiometric amounts of a material which will effectively remove the acid generated in the course of the reaction. Suitable acid binding reagents are anhydrous sodium or potassium carbonate or extra equivalents of the amine. The solvents of choice are non-protonic organic liquids such as toluene, chloroform, diethyl ether and dioxane. The preferred conditions are those in which components are allowed to react in toluene at 25° to 100°C. for 24 hours to 72 hours in the presence of potassium carbonate.

4. The secondary or primary amino derivatives of the compounds of this invention can be prepared by the various procedures under 1 above, if the amino group of the aminoalkanol is suitably blocked to reactivity by formation of a salt or, preferably, by substituting it with a readily removable blocking group such as trifluoroacetyl, carbobenzoxy or the like, followed by removal of the blocking group with a suitable technique such as mild acid hydrolysis or catalytic reduction.

Required intermediate dicarboxylic acids of this invention can also be prepared by a Friedel-Crafts acylation of dibenzothiophene employing oxalyl chloride as the acylating agent. There is obtained, by this method, a mixture of dibenzothiophene-2,6-dicarboxylic acid and dibenzothiophene-2,8-dicarboxylic acid. This mixture can be used directly in the subsequent esterification or amidation reactions or the mixture can be separated by fractional crystallization from dimethylformamide-water.

The dimethyl esters of dibenzothiophene-2,6-dicarboxylic acid and dibenzothiophene-2,8-dicarboxylic acid can be prepared by refluxing a mixture of the diacids in dry methanol saturated with hydrogen chloride. The mixed esters obtained in this manner can be separated by fractional crystallization or by column chromatography.

When the bis basic esters of this invention are prepared from a mixture of the dicarboxylic acids or reactive derivatives thereof the isomers can be separated by repeated crystallizations or the mixture of isomers may be used as antiviral agents. The relative amount of each isomer in the mixture can be determined by the following technique. The isomeric ratio is determined by transesterification to the corresponding dimethyl ester using methanolic potassium hydroxide and the ratio is quantitated by v.p.c. analysis of the mixture of dimethyl esters.

The following examples are illustrative of the invention.

EXAMPLE 1

PREPARATION OF BIS(3-DIETHYLAMINOPROPYL) DIBENZOTHIOPHENE-2,8-DICARBOXYLATE DIHYDROCHLORIDE

A solution of 7.6 g. (0.025 mole) of dibenzothiophene-2,8-dicarbonyl chloride and 6.5 g. (0.05 mole) of 3-diethylaminopropanol in 1 l. of chloroform was heated at reflux for two hours. The solution was concentrated to 500 ml., diluted with petroleum ether (75°–90°) and the precipitated solid was crystallized from methanol-isopropanol and finally from water-acetone to yield the product, m.p. 243°–245°, $\lambda_{max}^{EtOH}$ 254, $E_{1cm}^{1\%}$ 1380.

EXAMPLE 2

PREPARATION OF BIS(3-PIPERIDINOPROPYL) DIBENZOTHIOPHENE-2,6-(AND 2,8)-DICARBOXYLATE DIHYDROCHLORIDE MONOHYDRATE

A solution of 12.0 g. (0.038 mole) of a mixture of dibenzothiophene-2,6(and 2,8)-dicarbonyl chloride and 11.4 g. (0.08 mole) of 3-piperidinopropanol in 500 ml. of chloroform was heated at reflux for 24 hours. The solid which separated was treated with 25% aqueous sodium carbonate and the free base which resulted was extracted with ether, dried over anhydrous magnesium sulfate and was treated with ethereal hydrogen chloride. The dihydrochloride salt was recrystallized several times from methanol-ethyl acetate to yield the product consisting of approximately 75% of the 2,6-isomer and 25% of the 2,8-isomer, m.p. 248°–256°, $\lambda_{max}^{H_2O}$ 251, $E_{1cm}^{1\%}$ 873.

EXAMPLE 3

PREPARATION OF BIS(3-DIBUTYLAMINOPROPYL) DIBENZOTHIOPHENE-2,6(and 2,8)-DICARBOXYLATE DIHYDROCHLORIDE HEMIHYDRATE When 14.5 g. (0.078 mole) of 3-dibutylaminopropanol was used in place of 3-piperidinopropanol and the procedure of Example 2 was followed, the dibutylaminopropyl ester was obtained after an additional crystallization from butanone consisting of approximately 40% of the 2,6-isomer and 60% of the 2,8-isomer, m.p. 144°–146°, $\lambda_{max}^{H_2O}$ 252, $E_{1cm}^{1\%}$ 862.

EXAMPLE 4

Preparation of Bis(3-diisopentylaminopropyl) Dibenzothiophene-2,6(and 2,8)-Dicarboxylate Dihydrochloride H Preparation of Bis(-Dimethylamino--Dimethylpentyl) Dibenzothiophene-(and )-Dicarboxylate Dihydrochloride When 3-diisopentylaminopropanol was used in place of 3-piperidinopropanol and the procedure of Example 2 was followed, the product was obtained after an additional crystallization from ethanol-butanone-pentane consisting of approximately 70% of the 2,6-isomer and 30% of the 2,8-isomer, m.p. 110°–118°, $\lambda_{max}^{H_2O}$ 251, $E_{1cm}^{1\%}$ 700.

EXAMPLE 5

PREPARATION OF BIS(5-DIMETHYLAMINO-2,2-DIMETHYLPENTYL) DIBENZOTHIOPHENE-2,6(AND 2,8)-DICARBOXYLATE DIHYDROCHLORIDE

When 5-dimethylamino-2,2-dimethylpentanol was used in place of 3-piperidinopropanol and the procedure of Example 2 was followed, and after a final crystallization from methanol-butanone, the product was obtained consisting of approximately 88% of the 2,6-isomer and 12% of the 2,8-isomer, m.p. 245°–251°, $\lambda_{max}^{H_2O}$ 250, $E_{1cm}^{1\%}$ 890.

EXAMPLE 6

Preparation of Bis(2-Diethylaminoethyl) Dibenzothiophene-2,6(and 2,8)-Dicarboxylate -Dihydrochloride When 2-diethylaminoethanol was used in place of 3-piperidinopropanol and the procedure of Example 2 was followed, the product was obtained consisting of approximately 74% of the 2,6-isomer and 26% of the 2,8-isomer, m.p. 219°–225°, $\lambda_{max}^{H_2O}$ 252, $E_{1cm}^{1\%}$ 985.

EXAMPLE 7

Preparation of N,N'-Bis(3-Dibutylaminopropyl) Dibenzothiophene-2,8-Dicarboxamide Bis-Dihydrogen Citrate A solution of 9.3 g. (0.03 mole) of dibenzothiophene 2,8-dicarbonyl chloride and 11.2 g. (0.06 mole) of 3-dibutylaminopropylamine in 400 ml. of chloroform is heated at reflux for 4 hours. The chloroform solution is extracted with water, and the aqueous layer made basic with saturated sodium bicarbonate solution. The free base is extracted with ether, washed with water, dried over anhydrous magnesium sulfate and concentrated in vacuo. The residue is dissolved in methanol and converted to the dihydrogen citrate salt by treating the methanol solution with two equivalents of citric acid. The product is crystallized twice from methanolbutanone.

EXAMPLE 8

Preparation of N,N'-Bis(3-Diethylaminopropyl) Dibenzothiophene-2,8-Dicarboxamide Bis-Dihydrogen Citrate By the procedure of Example 7, one equivalent of dibenzothiophene-2,8-dicarbonyl chloride is allowed to react with two equivalents of 3-diethylaminopropylamine to give the product.

EXAMPLE 9

Preparation of Dibenzothiophene-2,6(and 2,8)-Dicarboxylic Acid

To 800 ml. of carbon disulfide cooled to −10° was added 56 g. (0.42 mole) of aluminum chloride and 36.8 g. (0.2 mole) of dibenzothiophene. To this mixture was added, with stirring, 101 g. (0.8 mole) of oxalyl chloride dissolved in 100 ml. of carbon disulfide and the resulting brown mixture was stirred at −10° for 4 hours and at 28°C. for 64 hours. The mixture was decomposed with cold dilute hydrochloric acid and after removal of carbon disulfide, the product was filtered and purified by extraction with dilute sodium hydroxide, filtration of the alkaline solution and conversion back to acid. The product does not melt below 320°.

EXAMPLE 10

Preparation of Dibenzothiophene-2,6(and 2,8)-Dicarbonyl Chloride

The diacid chloride was prepared by the thionyl chloride-pyridine method and purified by crystallization from toluene, m.p. 235°–237°.

EXAMPLE 11

Preparation of Dimethyl Dibenzothiophene-2,6(and 2,8)-Dicarboxylate

A mixture of 4.0 g. of dibenzothiophene-2,6-dicarboxylic acid and dibenzothiophene-2,8-dicarboxylic acid was refluxed in 200 ml. of anhydrous methanol saturated with hydrogen chloride for 48 hours. The product was obtained as a white crystalline solid on cooling, m.p. 145°–160°. The isomers were separated by fractional crystallization from methylene chloride. The 2,6-isomer melted at 184°–186° and the 2,8-isomer melted at 184.5°–187°. The isomers were further characterized by nmr.

EXAMPLE 12

This example illustrates antiviral activity of bis(3-dibutylaminopropyl) dibenzothiophene-2,6(and 2,8)-dicarboxylate dihydrochloride hemihydrate.

Two groups of mice were inoculated with a fatal dose (26 $LD_{50}$) of encephalomyocarditis. Each mouse weighed about 15 grams and each of the two groups of mice contained from 10 to 30 animals. The mice in one of the groups were treated both prophylactically and therapeutically by subcutaneous injections of bis(3-dibutylaminopropyl) dibenzothiophene-2,6(and 2,8)-dicarboxylate dihydrochloride hemihydrate. The injections were given 28, 22 and 2 hours prior to inoculation with the virus and 2, 20 and 26 hours after inoculation. The volume of each injection was 0.25 ml. and contained the active ingredient at a dosage level of 250 mg. per kg. dissolved in sterile water which also contained 0.15% of hydroxyethylcellulose. The control animals received a sham dosage of the same volume of the vehicle which did not contain the active ingredient. Observations over a 10-day period showed that the treated group of mice survived for a longer time than the controls.

EXAMPLE 13

An illustrative composition for a parenteral injection is the following wherein the quantities are on a weight to volume basis.

| (a) | Bis(3-piperidinopropyl) dibenzothiophene-2,6(and 2,8)-dicarboxylate dihydrochloride monohydrate | 200 mg. |
|---|---|---|
| (b) | Sodium chloride | q.s. |
| (c) | Water for injection to make | 10 ml. |

The composition is prepared by dissolving the active ingredient and sufficient sodium chloride in water for injection to render the solution isotonic. The composition may be dispensed in a single ampule containing 200 mg. of the active ingredient for multiple dosage or in 10 ampules for single dosage.

EXAMPLE 14

An illustrative composition for a parenteral injection is the following aqueous emulsion.

| Each ml. (milliliter) contains | Ingredient | Amount |
|---|---|---|
| 10 mg. | Bis(5-dimethylamino-2,2-dimethylphentyl) dibenzothiophene-2,6(and 2,8)-dicarboxylate dihydro- | 0.20 g. |

-continued

| Each ml. (milliliter) contains | Ingredient | Amount |
| --- | --- | --- |
| 100 mg. | chloride Polysorbate 80 | 2.000 g. |
| 0.0064 mg. | Sodium chloride | 0.128 g. |
| — | Water for injection, q.s. | 20.000 ml. |

The composition of Example 14 is prepared by: dissolving 0.64 grams of sodium chloride in 100 ml. of water for injection; mixing the Polysorbate 80 with the active ingredient; adding a sufficient solution of the sodium chloride in water to the active ingredient and Polysorbate to make 20 ml.; shaking the mixture; and then autoclaving it for 20 minutes at 110°C. at 15 p.s.i.g. steam pressure. The composition can be dispensed in a single ampule for multiple dosage or in 10 or 20 ampules for single dosages.

What is claimed is:

1. A compound of the formula

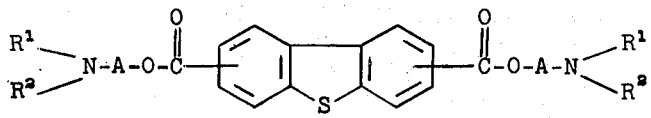

wherein the substituent groups

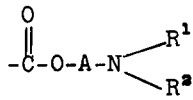

may be at the 2- and 6- or 8-positions and
A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;
B. each A is alkylene of 2 to about 8 carbon atoms and separates its adjacent O and amino nitrogen by an alkylene chain of at least 2 carbon atoms; or a pharmaceutically acceptable acid addition salt thereof.

2. A compound of claim 1 wherein each A is alkylene of 3 to 6 carbon atoms and each of the

groups is a tertiary amino group selected from di(-lower)-alkylamino, dialkenylamino, or each set of $R^1$ and $R^2$ together with the nitrogen to which they are attached is pyrrolidino, piperidino, N-(lower)alkylpiperazino or morpholino.

3. A compound of claim 2 wherein each of $R^1$ and $R^2$ is (lower)alkyl of 1 to 4 carbon atoms.

4. A compound of the formula

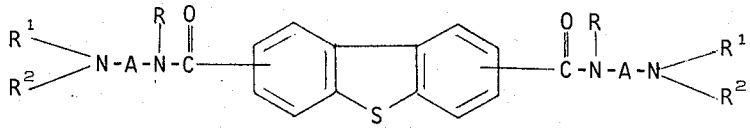

wherein the substituent groups

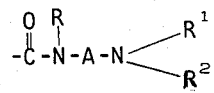

are at the 2- and 6- or 8-positions and
A. each of $R^1$ and $R^2$ is hydrogen, (lower)alkyl, cycloalkyl of 3 to 6 ring carbon atoms, alkenyl of 3 to 6 carbon atoms having the vinyl unsaturation in other than the 1-position of the alkenyl group, or each set of $R^1$ and $R^2$ taken together with the nitrogen atom to which they are attached is pyrrolidino, piperidino, N-(lower)alkylpiperazino, or morpholino;
B. each A is alkylene of 2 to about 8 carbon atoms and separates its adjacent amide nitrogen and amino nitrogen by an alkylene chain of at least 2 carbon atoms;
C. each R is hydrogen or (lower)alkyl, or a pharmaceutically acceptable acid addition salt thereof.

5. A compound of claim 4 wherein each R is hydrogen; each A is alkylene of 3 to 6 carbon atoms; and each of the

groups is a tertiary amino group selected from di(-lower)alkylamino, dialkenylamino, or each set of $R^1$ and $R^2$ together with the nitrogen to which they are attached is pyrrolidino, piperidino, N-(lower)alkylpiperazino or morpholino.

6. A compound of claim 5 wherein each of $R^1$ and $R^2$ is (lower)alkyl of 1 to 4 carbon atoms.

* * * * *